US006620853B1

(12) United States Patent
Shiff et al.

(10) Patent No.: US 6,620,853 B1
(45) Date of Patent: Sep. 16, 2003

(54) METHODS AND COMPOSITIONS FOR PREVENTION AND TREATMENT OF RESTENOSIS WITH NON-STEROIDAL ANTI-INFLAMMATORY DRUGS

(75) Inventors: Steven Shiff, New York, NY (US); Edward A. Fisher, Scarsdale, NY (US); Hayes M. Dansky, Larchmont, NY (US); Ernane Reis, New York, NY (US)

(73) Assignees: Mount Sinai School of Medicine, New York, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 09/456,633

(22) Filed: Dec. 8, 1999

Related U.S. Application Data

(63) Continuation-in-part of application No. 09/208,613, filed on Dec. 8, 1998, now Pat. No. 6,201,028.

(51) Int. Cl.[7] .................... A61K 31/192; A61K 31/405; A61K 31/5415; A61K 31/176; A61P 9/10

(52) U.S. Cl. .................... 514/708; 514/568; 514/569; 514/570; 514/420; 514/226.5; 514/824

(58) Field of Search .................... 514/340, 824, 514/929, 568–70, 708, 420, 226.5

(56) References Cited

U.S. PATENT DOCUMENTS

| 3,312,593 A | | 4/1967 | Sheen et al. |
|---|---|---|---|
| 5,591,199 A | * | 1/1997 | Porter et al. |
| 5,614,506 A | * | 3/1997 | Falk et al. |
| 5,643,943 A | | 7/1997 | Gamache et al. |
| 5,770,215 A | | 6/1998 | Moshyedi |
| 5,811,438 A | | 9/1998 | Hellberg et al. ............ 514/458 |
| 5,834,444 A | | 11/1998 | Falk et al. |

FOREIGN PATENT DOCUMENTS

| CA | 2 123 935 A | 5/1994 |
|---|---|---|
| CA | 2 127 573 A1 | 1/1996 |
| EP | 0 380 367 A1 | 1/1990 |
| WO | WO 93/13660 | 7/1993 |

OTHER PUBLICATIONS

Al–Meshal, Mohamed A. et al. Biopharmaceutics & Drug Disposition vol. 15 (No. 6) pp. 463–471 (1994).
Johnson, Anthony G. Drugs & Aging, vol. 12 (No. 1) pp. 17–27 (1998).
Lavelle, William G. et al. The New England Journal of Medicine vol. 321 (No. 3) pp. 183–185 (1989).
Cell 1992, 71: 343–353.
Circulation 1993, 88:A9.
Arteriosclerosis Thromb, 1994, 14:1873.
J. Cell Biol 1990, 111:2149.
Biochem. Pharmacol 1996, 52:237–245.
Adv. Drug Res 1977, 12: 90–245.
Cir Res 1990, 66:1755–1760.
Proc Natl Acad Sci USA 1993, 90:4591–4595.
Nature 1993, 801–809.
Science 1996, 272:685–688.
Abstract Zheng, Liquo, May 1998.
Abstract Parthasarthy, Sampath 1998, 1(1) pp. 45–51.
Rakes, Robert, Conn's Current Therapy Philadelphia W.B. Saundes Co. 1992, pp 504–509.

(List continued on next page.)

Primary Examiner—Edward J. Webman
(74) Attorney, Agent, or Firm—Klauber & Jackson

(57) ABSTRACT

Methods and compositions for the prevention and/or treatment of vascular restenosis, the methods comprising administering to individuals in need thereof, an effective amount of a non-steroidal anti-inflammatory drug alone or in combination with other conventional therapies to induce apoptosis, reduce proliferation, induce quiescence, inhibit cell migration, or influence cell differentiation of the cells in the vascular wall and or/induce hypolipidemia.

8 Claims, 2 Drawing Sheets

OTHER PUBLICATIONS

Abstract Falk et al., Oct. 1998.
Abstract Dennick, L.G., Jun. 1990.
Abstract Dincol et al., 1976 9(1) 11–15.
Abstract Vitic et al., 1979 15(3) pp. 504–506.
Abstract Willliams et al., 1992, 94(23), pp. 153–159.
Abstract Xue et al., 1998, 27(1) 36–37.
Abstract Rogalla et al., Feb. 1994.
Abstract 1997, 337(6) 365–372.
Abstract Konneh, et al. 1995, 113(1) 29–39.
Abstract Demopoulous Jul. 1993.
Abstract Lee et al., 1996, 37(3) 32–322.
Abstract Herbert et al., 1998, 80(3) 512–518.

* cited by examiner

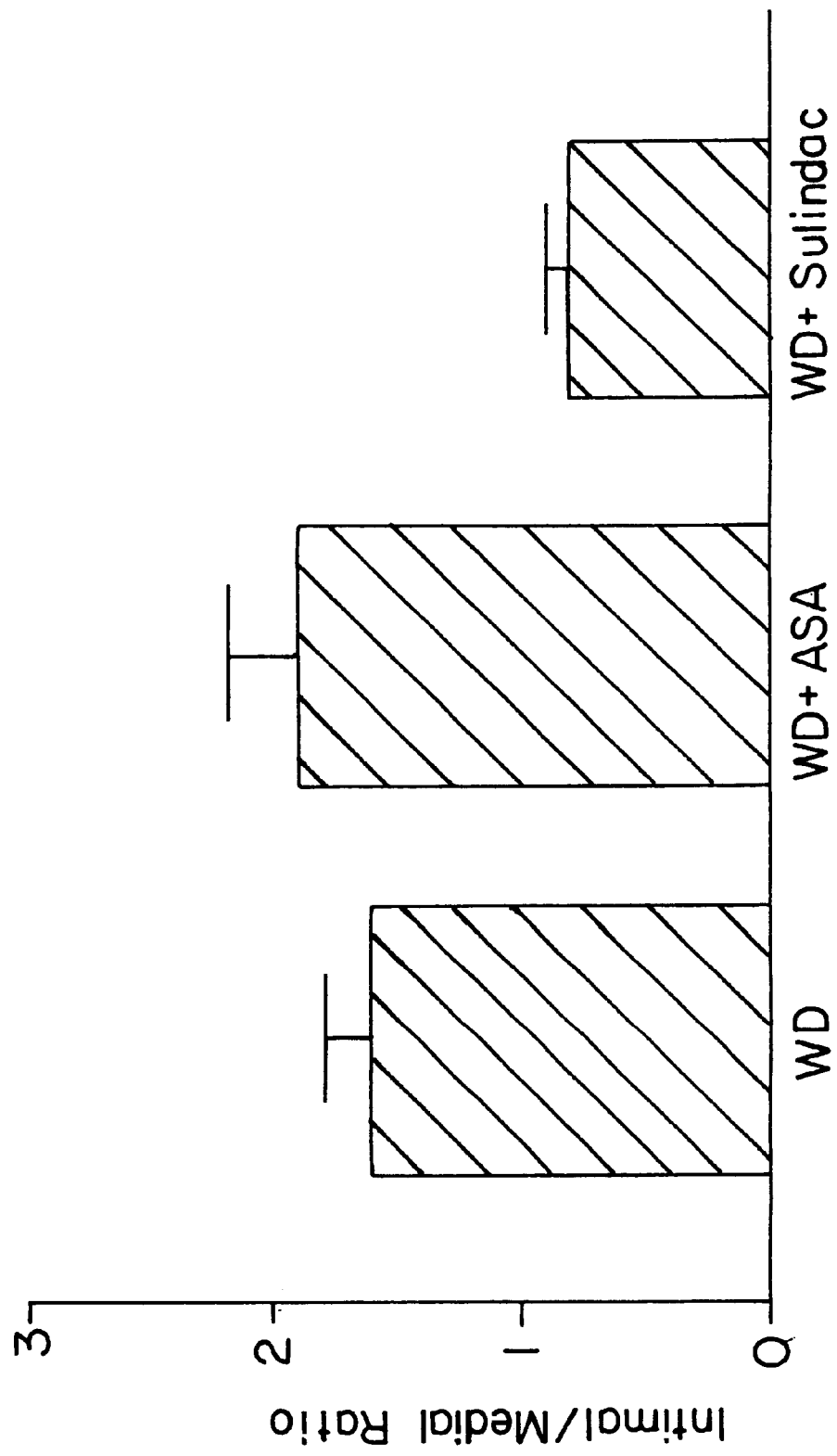

METHODS AND COMPOSITIONS FOR PREVENTION AND TREATMENT OF RESTENOSIS WITH NON-STEROIDAL ANTI-INFLAMMATORY DRUGS

CROSS-REFERENCE TO RELATED APPLICATIONS

This Application is a Continuation-In-Part of application Ser. No. 09/208,613 filed Dec. 8, 1998 now U.S. Pat. No. 6,201,028, which is hereby incorporated by reference specifically for disclosure on restenosis and in general, in its entirety.

1. INTRODUCTION

The present invention relates to methods and compositions for the prevention and treatment of cardiovascular disease, specifically, but not limited to, restenosis and arterial inflammation with the administration of non-steroidal anti-inflammatory drugs (NSAIDs). The present invention relates to methods and compositions for preventing and/or treating restenosis in mammals, by inducing or stimulating apoptosis, reducing proliferation, inducing quiescence, inhibiting cell migration, altering argiogenesis, altering extracellular matrix formation, or influencing cell differentiation of the cells of the vessel wall that contribute to arterial lesions. In particular, the methods and compositions of the invention are useful in the stimulation of cell death and/or the inhibition of the robust response to arterial injury by inhibition of the proliferation or migration of vascular cells or other target cells that contribute to arterial lesions formation.

2. BACKGROUND OF THE INVENTION

Cardiovascular disease, including, but not limited to, atheroslerosis, ischemia, reperfusion, hypertension, restenosis and arterial inflammation, is a major health risk, throughout the industrialized world. Atherosclerosis, the most prevalent of cardiovascular diseases, is the principal cause of heart attack, stroke, gangrene, clandication, and gangrene of the extremities. It is a complex disease involving many cell types and molecular factors. Ross, 1993, Nature 362:801–809. Under normal circumstances, a protective response is mounted when there is injury to the endothelium and smooth muscle cells of the wall of the artery, and consists of formation of fatty and fibrous lesions or plaques, accompanied by inflammation. The advanced lesions of atherosclerosis may occlude the artery affected, and result from an excessive inflammatory response to different forms of injury. For example, shear stresses are thought to be responsive for the frequent occurrence of atherosclerotic plaques in regions of the circulatory system where turbulent blood flow occurs, such as branch points and irregular structures.

Ischemia is a condition when there is a lack of oxygen supply in tissues of organs due to inadequate perfusion due to atheroslerotic or restenotic lesions, stroke, or anemia, to name a few. The most common cause of ischemia in the heart is atherosclerotic disease of the epicardial coronary arteries. Myocardial ischemia can also occur if myocardial oxygen demands are abnormally increased, due to hypertension or aortic stenosis.

Since an excessive inflammatory—fibroproliferative response is implicated in atherosclerosis and ischemia, the expression of certain factors such as growth factors, cytokines and lipids involved in inflammation and cell proliferation, has been investigated. For example, the expression of platelet derived growth factor (PDGF) was studied in rats during repair of arterial injury (Majesky et al., 1990, J. Cell. Biol. III;2149); the expression of insulin-like growth factor-I(IGF-I) was studied after balloon deendothelialization of the at aorta (Corceck et al., 1990, Circulation Research 66:1755–1760); and in bovine aortic endothelial cells subjected to fluid shear stress (Resnick et al., 1993, Proc. Natl. Acad. Sci. USA 90:4591–4595).

The principal surgical approaches to the treatment of acute or chronic ischemic atherosclerosis are percutaneous translumenal angioplasty (PCTA), bypass grafting, and endarterectomy. Revasularization procedures are frequently used as interventions in vascular disease, including in the unstable coronary syndromes. For example, PCTA and related procedures, including stent placement, are performed on over 400,000 patients in the United States alone. Among patients who have undergone initially successful angioplasty, the outcome over the first 6–12 months is influenced primarily by the development of recurrent stenosis or "restenosis" at treated sites. The failure rate after these approaches due to restenosis, in which the occlusions recur and often become even worse, is very high (30–50%). It appears that much of the restenosis is due to further inflammation, smooth muscle accumulation and thrombosis or other factors. The incidence of restenosis has essentially remained unchanged since the introduction of angioplastic techniques, and is approximately 30–50%, despite treatment with aspirin and related compounds that inhibit platelet aggregation. In fact, recent figures showed 30% of angioplasty patients require a revascularization procedure within one year of their original procedure due to restenosis, resulting in approximately two billion dollars in health care charges on top of the initial costs for surgery.

Other studies have focused on the expression of genes and gene products presumed to be involved in the processes leading to restenosis and inflammatory proliferative reactions. However, such approaches cannot identify the full range of gene products that are involved in the disease process; and much less identify those which may serve as therapeutic targets for prevention and treatment of restenosis and inflammatory proliferative diseases.

3. SUMMARY OF THE INVENTION

In accordance with the invention, methods and compositions are provided for the prevention and treatment of restenosis by administering non-steroidal anti-inflammatory drugs. The compositions include NSAIDs alone or in combination with lipid lowering agents or diets or antioxidants or angioplastic procedures or other surgical manipulations. The preventive and/or treatment methods can involve inducing apoptosis, reducing proliferation, inducing quiescence, inhibiting macrophage migration, or influencing cell differentiation, and/or clearance of lipoproteins to thereby prevent and/or treat arterial lesions and provide a variety of health benefits.

The present invention can provide a method of preventing)arterial lesions and restenosis by applying NSAIDs which induce apoptosis, reduce proliferation, induce quiescence, inhibit macrophage and smooth muscle cell migration, or influence cell differentiation in the vessel wall. The method can include subjecting the vascular cells to an effective amount of NSAIDs to trigger and induce programmed cell death, reduce proliferation, induce quiescence, inhibit macrophage and smooth muscle cell migration, or influence cell differentiation and prevent occlusive or thrombotic events in arteries or veins.

The present invention can also provide a therapeutic method for the treatment of arterial lesions and restenosis, associated with apoptosis, proliferation, monocyte/macrophage and smooth muscle cell migration, or differentiation of vascular cells by administering an effective amount of an NSAID to induce apoptosis, reduce proliferation, induce quiescence, inhibit macrophage and smooth muscle cell migration, or influence cell differentiation of cells that contribute to atherosclerosis. In accordance with the invention, an effective amount of one or more NSAID is administered to prevent and/or treat a variety of atherosclerotic conditions.

According to an additional aspect of the present invention, there is provided a method to induce apoptosis, reduce proliferation, induce quiescence, inhibit macrophage and smooth muscle cell migration, or influence cell differentiation of cells that contribute to a complex or unstable plaque in restenosis by administering NSAIDs along with an antithrombotic therapy, including the administration of an effective amount of an antithrombotic agent such as heparin or warfarin.

According to yet another, aspect of the present invention, there is provided a method to induce apoptosis, reduce proliferation, induce quiescence, inhibit macrophage and smooth muscle cell migration, or influence cell differentiation of cells that contribute to restenosis by administering NSAIDs along with antioxidant therapy, including the administration of an effective amount of an antioxidant such as vitamin A, vitamin E, N-acetylcysteine, glutathione, vitamin C, and/or magnesium gluconate.

According to yet another aspect of the present invention, there is provided a method to induce apoptosis of cells that contribute to atherosclerosis including the application of NSAIDs in combination with a conventional therapeutic regimen including by-pass surgery, angioplasty, beta-blocker therapy, calcium channel antagonists, magnesium, thrombolytic therapy, antithrombotic therapy or drug therapy.

In accordance with the invention, compositions for the induction of apoptosis, reduction of proliferation, induction of quiescence, inhibition of macrophage and smooth muscle cell migration, or influence on cell differentiation in cells that contribute to restenosis are also provided and include NSAIDS used alone or in combination with conventional therapeutic regimens used to prevent and/or treat arterial or venous lesions or restenosis.

The present invention is based on the (unexpected discovery that NSAIDs are effective in inducing apoptosis, reducing proliferation, inhibiting migration, or influencing differentiation of cells that contribute to restenosis.

It is the object of the present invention to provide compositions and/or methods for inducing apoptosis, reducing proliferation, inhibiting migration, or influencing differentiation of cells that contribute to restenosis.

It is the object of the present invention to provide compositions and/or methods for inducing cell quiescence, reducing proliferation, inhibiting migration, or influencing differentiation in the cells of the vessel wall that contribute to arterial lesions and restenosis.

It is the object of the present invention to provide compositions and/or therapeutic methods for preventing recurrence of atherosclerosis after procedures designed to increase coronary artery blood flow, such as by-pass surgery, reperfusion or angioplasty.

It is also an object of the present invention to provide compositions and/or methods for inducing apoptosis and cell quiescence in cells of the vessel wall using NSAIDs alone or in combination with an effective amount of one or more conventional therapies or antioxidants.

Still other objects and advantages of the invention will in part be obvious and will in part be apparent from the specification and working examples described herein.

4. BRIEF DESCRIPTION OF DRAWINGS

For a fuller understanding of the invention, reference is made to the following description taken in connection with the accompanying drawings, in which:

FIG. 2 is a diagram illustrating the average Intimal/Medial Ratio in apoE-knockout (apoE-KO) mice which were maintained on a "western diet" (WD) alone or a "western diet & aspirin (ASA) (300 mg/kg food/day) or a "western diet"+Sulindac (300 mg/kg food/day). The feeding period started one week prior to and ended four weeks after wire injury of the femoral artery.

5. DETAILED DESCRIPTION OF THE INVENTION

Figure 1:
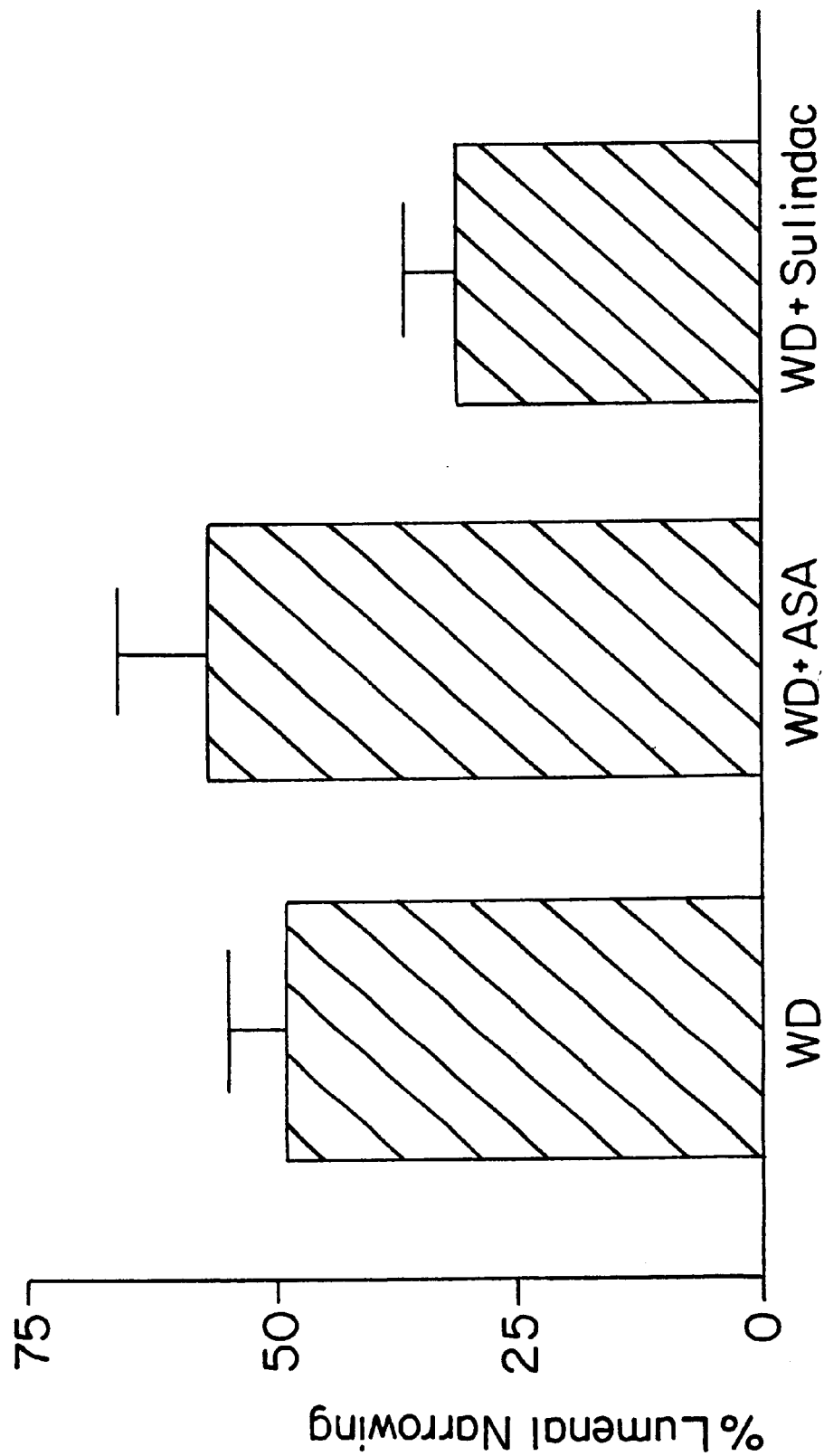
FIG. 1 is a diagram illustrating the average % lumenal narrowing in apoE-knockout mice which were maintained on a "western diet" alone or a "western diet"+aspirin (300 mg/kg food/day) or a "western diet" + Sulindac (300 mg/kg food/day). The feeding period started one week prior to and ended four weeks after wire injury of the femoral artery.

The present invention generally pertains to compositions and novel methods for preventing and treating arterial lesions and restenosis using one or more NSAIDs in an effective amount for inducing apoptosis, reducing proliferation, inhibiting migration, or influencing cell differentiation in treated cells. The restenosis prevention and therapeutic methods of the invention are fundamentally based upon a newly-discovered effect of NSAIDs on apoptosis, proliferation, migration or differentiation of vascular cells, and for inducing quiescence in the cells of the vessel wall.

5.1 Restenosis Following Angioplasty

Following a coronary intervention such as angioplasty, the artery may close in the late phase due to a process of wound healing called restenosis. Although the size of the lumen decreases following almost all intervention, restenosis is defined as a compromise of the lumen that is felt to approach an obstruction that could result in hemodynamic compromise. This degree of narrowing is usually arbitrarily defined as a narrowing of the lumen that is equal to or exceeds 50% of the lumen diameter in the adjacent normal appearing segments.

Revascularization procedures are frequently used as interventions in vascular disease, including the unstable coronary syndromes. For example, percutaneous translumenal coronary angioplasty and related procedures, including stent placement, are performed on over 400,000 patients in the United States alone. Among patients who have undergone initially successful angioplasty, the outcome over the first 6–12 months is influenced primarily by the development of recurrent stenosis or restenosis at treated sites.

The incidence of restenosis has essentially remained unchanged since the introduction of angioplastic techniques, and is approximately 30–50%, despite treatment with aspirin and related compounds that inhibit platelet aggregation. In general, 30% of angioplasty patients require a revascularization procedure within one year of their procedure due to restenosis, resulting in approximately two billion dollars in health care charges on top of the initial costs. Hence, major research efforts are being directed towards identifying the mechanisms involved in the prevention and treatment of restenosis.

Essentially, restenosis represents a robust response to vessel injury characterized by an expansion of the cell mass of the vascular wall through increased proliferation or decreased apoptosis of cells in the vessel wall. In order to understand the mechanism of restenosis, one must understand the mechanism by which arteries are opened. In balloon angioplasty, the balloon is inflated in a heavily diseased segment of the artery with thick concentric plaque. The arterial lumen is narrowed. However, the external dimensions of the artery may actually be wider than normal due to the radial growth of the space occupying plaque. When the balloon is inflated, the lumen is expanded and the external dimension of the artery is expanded as well. Cracks and splits develop in the plaque and arterial wall, for example at the junction of the plaque and the less involved arterial wall at points where less compliant tissue such as calcified or densely fibrotic plaque components exist. Splits may extend into the plaque material, into the media, or through the media into the adventitial surface.

Therefore, there are three components in restenosis: 1) the elastic recoil that occurs promptly after the overstretch of the artery which is approximately 50% of the cross-sectional area; 2) the intimal proliferation resulting in new tissue growth occupying the cracks and tears in the vessel wall and growing to reobstruct the artery beginning within days after angioplasty and continuing for weeks or months; and 3) the mechanism analogous to wound contracture, i.e., the entire artery may become contracted so that the external elastic lamina occupies a smaller circumference than it did following the procedure, and may account for up to 60% to 65% of the lumen loss. Damage to the arterial wall and its surrounding tissues results in transformation of cells in the media and in the adventitia so that they are signaled to proliferate, migrate, even inhibit and elaborate extracellular matrix. These cells may then undergo phenotypic transformation and become cells capable of causing contracture.

Attempts to control restenosis have been aimed at a wide array of targets. For example, agents tested were anticoagulants (heparin, coumadin), antiplatelet agents (aspirin, persantine, thromboxane inhibitors), antispasmodics (nifedipine, diltiazem) and lipid-lowering agents (lovastatin, omega-3 fatty acids).

Most of these were evaluated in single-center trials and although powerful effects have been observed in some studies, a there was a problem of dosing. Because of the problem of achieving adequate concentrations in the local environments with systemic drug therapy, experimental effects have concentrated on the local delivery of drugs. Methods of retaining a drug, including the use of drug-containing polymer-coated stents or other devices, have been advocated. Methods for achieving increased arterial lumen size with new devices have been introduced, for example, atherectomy or tissue removing techniques, and stenting or vascular splinting techniques.

While stents have reduced the restenosis rate for suitable lesions, restenosis within the stent remains a problem with restenosis rates from 31% to 54%.

5.2 Risk Factors
5.2.1 Cell Proliferation

The structural organization of a vessel wall consists of three layers: the intima, the media, and the adventitia. The intima is a single continuous layer of endothelial cells and associated basement membrane. The media is a layer of smooth muscle cells separated from the intima by a sheet of elastic fibers, the internal elastic lamina. The external elastic lamina forms the border between the media and the adventitia. The response to injury hypothesis of atherosclerosis postulates that injury to the endothelium is the primary event in the formation of an atherosclerotic lesion. Smooth muscle cells then migrate from the media into the intima through fenestrae in the internal elastic lamina and undergo active proliferation within the intima. High levels of cholesterol and oxidized lipoproteins trigger and stimulate the proliferation of smooth muscle cells. Adherence of platelets to exposed connective tissue may cause the formation of platelet aggregates or microthrombi. If the lesion progresses further, fibrosis, lipid deposition, necrosis and calcification may ensue to yield a complicated plaque. The atherogenic process involves the proliferation, in the arterial wall, of some major cell types found in the plaque: vascular smooth muscle cells and macrophages. In both primary and re-stenoic or recurrent atherosclerotic lesions however, vascular smooth muscle cells tend to be the earliest and most robust responders to atherogenic stimuli, such as hyperlipidemia and endothelial cell damage. Thus, as proliferation of vascular smooth muscle cells increases in response to specific physiologic signals, there is a need to balance cell renewal and cell death in order to conserve the total cell mass in the vessel wall. If stimuli for proliferation continue to be exerted, for example, through chronic hyperlipidemia, then eventually cell death or apoptosis can no longer offset the inducement to cell proliferation resulting in the vessel wall thickness becoming dysregulated. The end result is that the vessel wall thickness expands and the lumen of the artery narrows, resulting in the secondary complications of atherosclerosis, for example, reduced blood flow to the organs downstream of the stenotic vessel.

5.2.2. Apoptosis

Apoptosis, a genetically regulated form of cell death, is a general property of most if not all cells. It is necessary in tissues of multicellular organisms to achieve an adequate balance between the sufficient survival of cells and the overwhelming proliferation and expansion of the cell mass, i.e., cell mass homeostasis.

From the perspective of arterial lesions and atherosclerosis, apoptosis or programmed cell death may be both a mechanism which suppresses plaque formation and as a predominant pathway in anti-atherosclerotic therapy. Two major endogenous regulators of apoptosis have been identified, for example, the wild-type p53 protein which functions as an inducer of cell death especially in response to DNA damaging events and reciprocally, Bcl-2 which has an important antiapoptotic function (Nature 1992, 358:15; and Cell 1995, 80:285).

It is important to note that induction of apoptosis in the atherosclerotic lesion may not always be beneficial; for example, in a complex plaque, apoptosis of lipid-laden macrophages and monocytes may result in release of oxidized pro-thrombotic lipid or lipid-associated materials into the extracellular space which in turn may result in formation of occlusive thrombi. Thus, the effects of apoptosis may be anti- or pro-atherogenic depending on the evolution of or the stage of development of the arterial lesion. For example, since the early events of plaque formation depend on proliferation of vascular smooth muscle cells, increasing apoptosis of those cells with NSAIDs, before the arterial wall thickness exceeds a threshold level reduces the extent of lesions and thus improves the vessel patency. On the other hand, if a lesion were reasonably well-established, increasing apoptosis may destabilize the plaque, and result in myocardial inschemia or infarction.

In a severely stenotic vessel that has been subjected to angioplasty, increasing apoptosis with NSAIDs prolongs the time the treated vessel remains patent since an early event in re-stenosis is proliferation of vascular smooth muscle cells.

Cellular antioxidant defense mechanisms such as the reactive-oxygen scavenger enzymes superoxide dismutase, glutathione peroxidase and catalase can control apoptosis. For example, there is evidence that Bcl-2 inhibits apoptosis through the regulation of glutathione peroxidase. Thus, the present invention also includes a method for inducing apoptosis in vascular smooth muscle cells using a combination of NSAIDs and antioxidant therapy. Suitable antioxidants include, but are not limited to, one or more of N-acetylcysteine, vitamin E, glutathione, vitamin C and/or magnesium gluconate. Patient dosages for administration would vary according to the antioxidant used, for example, the adult dose for vitamin E would range from 200 I.U. to 1000 I.U. per day.

5.3 Non-Steroidal Anti-inflammatory Drugs

Non-steroidal anti-inflammatory drugs have anti-inflammatory, analgesic and antipyretic activities. They are used clinically for the treatment of patients with acute arthritis, chronic arthritis such as rheumatoid arthritis, osteoarthritis, gouty arthritis, ankylosing spondylitis, tendonitis, bursitis and inflammatory arthritis. In addition to their therapeutic use in these conditions, NSAIDs have been found to reduce the risk of development and mortality of oesophageal, gastric, and colorectal cancer.

5.3.1. Cyclooxygenase Inhibitors

Members of the structurally diverse class of drugs known as NSAIDs are thought to exert their anti-inflammatory, antipyretic and analgesic effects by inhibition of cyclooxygenases, the rate-limiting enzymes that catalyze the formation of prostaglandin precursors from arachidonic acid. Prostaglandins play a role in the control of cell proliferation and regulation of immune functions. However, doses of NSAIDs required to suppress inflammation may exceed substantially the doses necessary to inhibit prostaglandin synthesis, suggesting that the anti-inflammatory properties of these drugs may be achieved through additional mechanisms. For example, NSAIDs including, but not limited to aspirin, indomethacin, naproxen, Sulindac and piroxicam reduced proliferation and altered morphology of HT-29 human colon adenocarcinoma cells. A common property of NSAIDs to decrease tumor cell proliferation, alter morphology, cause cells to accumulate in the $G_0/G_1$ phase of the cell cycle and increase the rate of apoptosis, tends to suggest common targets of the drugs of the NSAIDs tested (aspirin, indomethacin, Sulindac and its metabolites, naproxen and piroxicam). In addition, certain NSAIDs may act independent of their ability or inability to inhibit cyclooxygenase. In the HCT-15 cultured colon cancer cell line the NSAIDs, Sulindac and piroxicam exerted their antiproliferative effect independent of prostaglandin synthesis (Biochem. Pharmacol. 1996, 52:237–245).

Heretofore, the only NSAID recommended for use in the treatment of coronary artery disease has been aspirin. Aspirin has become a critical component of acute myocardial therapy. Aspirin irreversibly acetylates the platelet cycolooxygenase enzyme and elicits its effect for the life of the platelet. Aspirin has also been used for secondary prevention of recurrent cardiovascular events following acute myocardial infarction. In the case of platelets, even a small dose of aspirin inhibits prostaglandin and thromboxane production.

In the present invention, administration of NSAIDs resulted in inhibition of development of atherosclerotic lesions, and in reducing the plasma levels of cholesterol, and in preventing restenosis. More specifically, administration of Sulindac to ApoE-deficient mice maintained on a western diet significantly inhibited the development of atherosclerotic lesion and restenosis. Unexpectedly, administration of Sulindac also reduced the level of cholesterol in the plasma. See infra, Section 6. In addition, Sulindac also inhibited restenosis. See infra, Section 7.

Sulindac (Clinoril®) is a prodrug that is metabolized after p.o. administration to either a sulfide or sulfone derivative. The sulfide is known to be a potent inhibitory agent of cyclooxygenase and is exclusively responsible for the anti-inflammatory properties of Sulindac. The sulfone does not inhibit cyclooxygenase and does not have anti-inflammatory properties. (Adv. Drug Res. 1977, 12:90–245).

Similarly administration of aspirin to ApoE-deficient mice maintained on a western diet inhibited the atherosclerotic index but to a lesser extent than observed in the group treated with Sulindac. Aspirin also unexpectedly reduced the level of cholesterol in the plasma. See infra, Section 6. Thus, aspirin and Sulindac and NSAIDs in general are useful for the prevention and treatment of hyperlipidemia and atherosclerotic lesions and restenosis.

5.3.2. Choice of NSAIDs

The present invention provides a number of different structurally diverse class of drugs known as NSAIDs which have the ability to induce apoptosis, reduce proliferation, inhibit migration, or influence cell differentiation in cells of the vascular wall and which increase the clearance of cholesterol and thereby to lower plasma cholesterol levels, for example, Sulindac, Sulindac sulfide, Sulindac sulfone, aspirin, indomethacin, ibuprofen, meclofenamic acid, flurbiprofen, naproxen or piroxicam.

5.4 Pharmaceutical Preparations and Methods of Administration

The NSAIDs that induce apoptosis, reduce proliferation, inhibit migration, or influence cell differentiation of cells in vessel walls and/or induce hypolipidemia, can be administered to a patient at therapeutically effective doses to prevent or treat atherosclerotic lesions or restenosis. A therapeutically effective dose refers to that amount of the compound sufficient to result in prevention or treatment of symptoms or complications of atherosclerosis.

5.4.1. Dosage and Formulation

Pharmaceutical compositions of NSAIDs may include the currently available formulations or may be formulated in different proportions in combination, using one or more physiologically acceptable carriers or excipients.

Thus, the NSAIDs alone or in combination with other NSAIDs, antioxidants or other conventional therapies e.g., the cholesterol lowering drugs, may be formulated with pharmaceutically compatible counterions, a form in which they are merely water-soluble.

The pharmaceutical compounds may be administered intravenously, intraarterially, intraperitioneally, subcutaneously, sublingually, intramuscularly, intraperitoneally, intrathecally, orally, rectally, topically or by aerosol.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparation for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

6.0 EXAMPLE: Effects of Sulindac and Other NSAIDs on Reducing Restenosis Following Arterial Revasularization Procedures

6.1 The Apo-E Deficient Mouse Model

The Apo-E deficient mouse is the first mouse model of atherosclerosis with pathology similar to that of human atherosclerosis (Cell 1992, 71:343–353). Serum cholesterol levels in the mice maintained on a chow diet are five times higher than those of control littermates. Apo-E, which is made primarily in the liver, is a surface constituent of lipoprotein particles and a ligand for lipoprotein recognition and clearance by lipoprotein receptors (Science 1996, 272:685–688). ApoE-deficient mice have delayed clearance of lipoproteins, and on a low-cholesterol, low-fat diet, their cholesterol levels reach 400 to 600 mg/dl as a result of accumulation of chylomicron and very low-density lipoprotein (VLDL) remnants enriched in esterified and free cholesterol (Circulation 1993, 88:A9). These mice develop not only fatty streaks but also widespread fibrous plaque lesions at vascular sites typically affected in human atherosclerosis (Arterioscier. Thromb. 1994, 14;1873). Lesions form at the base of the aorta and the lesser curvature of the thoracic aorta, at the branch points of the carotid, intercostal, mesenteric, renal and iliac arteries, and in the proximal coronary, carotid, femoral, subclavian, and brachiocephalic arteries. Lesions begin at 5 to 6 weeks of age with monocyte attachment to the endothelium in lesion-prone areas and transendothelial migration. Fatty streak lesions begin to appear at 10 weeks, and intermediate lesions containing foam cells and spindle-shaped smooth muscle cells appear at 15 weeks. Fibrous plaques appear after 20 weeks and consist of a necrotic core covered by a fibrous cap of smooth muscle cells surrounded by elastic fibers and collagen. In older mice, fibrous plaques progress. In some advanced lesions there is partial destruction of underlying medial cells with occasional aneurysm formation, and in others calcification occurs in the fibrous tissue. Extensive fibro-proliferation can narrow the lumen, even to the point of occlusion of vessels.

Atherosclerosis can be exacerbated by a high-cholesterol or high-fat diet. This effect is mimicked in the ApoE-deficient mice when these mice are fed a western-type diet as described below in Section 6.

The Apolipoprotein E knock-out mouse model is a valuable animal model to test the effect of NSAIDs on apoptosis, proliferation, quiescence, migration and differentiation of cells that contribute to atherosclerosis. ApoE is an apoprotein on the surface of atherogenic lipoproteins that serves as a ligand for certain receptors in key tissues. ApoE-induced signaling via these receptors, particularly by the hepatic LDL receptor, induces the removal of ApoE-containing lipoprotein particles from the plasma. When both copies of ApoE are knocked-out by gene targeting, the atherogenic proteins, e.g., VLDL and chylomicron remnants accumulate in the plasma and are deposited at accelerated rates in vascular tissue. The result is the relatively rapid formation of complex atherosclerotic lesions in the aorta, which have the essential characteristics of human plaques, namely proliferation and migration of vascular smooth muscle cells and macrophage foam cell formation. This model is highly suitable for pre-clinical screening of drugs, metabolic factors and other modalities aimed at preventing and/or treating atherogenesis and restenosis.

6.2 The Novel Mouse Model of Restenosis

We have developed a new mouse model of studying restenosis, in which the injury of the femoral artery is accomplished by the manipulation of wire stent which is introduced into the femoral artery first and then removed.

Briefly, the mouse is anesthetized with pentobarbital and the femoral artery is exposed by cutting the skin in the femoral region carefully. An angioplastz guide wire obtained from Advanced Cardiovascular Systems, Tameaila, Calif. of approximately 100 mm in length and 0.25 mm in diameter is then carefully inserted into the femoral artery, gently manipulated to simulate the arterial revascularization procedures used in humans, and removed. The bleeding is stopped by ligation. The skin fold is restored by sutures.

By one month after injury maximum restenosis is measured is achieved. The degree of restenosis is measured by two indices, the intima/media (I/M) ratio and the percentage of lumenal narrowing. Before injury, the mouse artery is fully patent, i.e., it has 0% narrowing, and the thickness of the media far exceeds that of the intima, so that the I/M ratio is close to zero. After injury, there is an expansion of the medial smooth muscle population and migration of smooth muscle cells into, and thereby thickening, the intima, transferring it into a "neo-intima" as shown in FIG. 2. This newly devised model has proven to be useful in testing drugs which have inhibiting effects on restenosis.

7.0 Effects of Sulindac and Aspirin on Restenosis in APO-E DEFICIENT MICE.

ApoE knockout mice maintained on the Western Diet with or without additional Sulindac (300 mg/kg) for 17 weeks were subjected to acute mechanical arterial injury. Four weeks later, they were sacrificed and the injured area was examined. FIG. 4 shows cross-sectional views of (A) the control non-injured femoral artery, (B) one hour after injuring the femoral artery, (C) 24 hours after injuring the femoral artery, (D) one week after injuring the femoral artery, (E) two weeks after injuring the femoral artery and (F) four weeks after injuring the femoral artery. Results obtained indicate increasing smooth muscle cell proliferation and arterial narrowing after mechanical injury, with time. However, in the mice receiving Sulindac in the diet, there was much less proliferation of smooth muscle cells recorded and the narrowing of the artery was not as marked, as compared with corresponding specimens from the control group. (FIG. 4). These results demonstrate that Sulindac treated animals exhibit a paucity of smooth muscle cell proliferation and arterial narrowing after mechanical injury. This demonstrates a strong inhibitory effect of the drug on vascular cell proliferation.

7.1. Materials and Method

Thirty six week old ApoE-knockout mice were used and given the following dietary regimen and treatment: Group 1-western type diet (containing 42% by calories % fat and 0.15% (w/w) cholesterol); Group 2-western type diet plus aspirin at a concentration of 300 mg/kg diet/day and Group 3-western type diet plus Sulindac at a concentration of 300 mg/kg diet/day. The diets were started 1 week before the femoral artery injury and continued for a further 4 weeks. There was no effect of the treatment at this dosage regimen on body weight. The body weight was monitored on a weekly basis.

Aspirin was chosen as a control NSAID to test whether any effects observed with Sulindac were due to its NSAID antiflammatory effects or were specific to the unique properties of Sulindac per se.

Four weeks after injury, the mice were sacrificed and the arteries examiner by routine histopathologial techniques. Using digitized images and the appropriate computer software, the I/M ratios and the degree of narrowing were determined.

Results obtained demonstrate that the combination of Sulindac with the western diet marked inhibited restenosis compared with the groups kept on the western diet alone or the western diet plus aspirin. This conclusion was supported by data the post injury Lumen Narrowing in Apo KO mice (FIG. 2). The present embodiment describes Sulindac and aspirin effects in the restenosis mouse model of the invention.

The present invention is not to be limited in scope by the embodiments disclosed in the example which are intended as an illustration of one aspect of the invention and any methods which are functionally equivalent and within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the compositions set forth without departing from the spirit and scope of the invention, it is intended that all matter contained in the above description and shown in the accompanying drawings shall be interpreted as illustrative and not in a limiting sense. It is also to be understood that the following claims are intended to cover all of the generic and specific features of the invention herein described and all statements of the scope of the invention which, as a matter of language, might be said to fall there between.

What is claimed is:

1. A method of preventing development of vascular restenosis in an individual having a region of nonproliferating and proliferating cells, the method comprising administering to the individual an effective amount of a non-steroidal anti-inflammatory drug to induce apoptosis of the proliferating cells.

2. The method according to claim 1, wherein the cells comprise vascular smooth muscle cells, endothelial cells or macrophages.

3. The method according to claim 1, wherein the non-steroidal anti-inflammatory drug is selected from the group consisting of sulindac, sulindac sulfide, sulindac sulfone, aspirin, indomethacin, ibuprofen, meclofenamic acid, flurbiprofen, naproxen and piroxicam.

4. The method according to claim 1, wherein an effective amount of non-steroidal anti-inflammatory drug is administered in an individual having undergone a vascular vessel revascularization procedure.

5. The method according to claim 1, wherein an effective amount of non-steroidal anti-inflammatory drug is administered in an individual having undergone angioplasty.

6. The method according to claim 1, further comprising administration of an antioxidant.

7. The method according to claim 6, comprising administration of an effective amount of at least one antioxidant selected from the group consisting of vitamin A, vitamin E, N-acetylcysteine, glutathione, vitamin C, and magnesium gluconate.

8. The method according to claim 1, further comprising administration of a lipid lowering agent.

* * * * *